(12) United States Patent
Güth et al.

(10) Patent No.: US 8,915,143 B2
(45) Date of Patent: Dec. 23, 2014

(54) COMBINATION ULTRASENSITIVE FORCE TRANSDUCER AND GRABBING DEVICE FOR FORCE AND STRAIN MEASUREMENT FROM SINGLE CELLS

(75) Inventors: Konrad Güth, Heidelberg (DE); Harm J. Knot, Haren (NL); Harry Fein, Nokomis, FL (US)

(73) Assignee: World Precision Instruments, Inc., Sarasota, FL (US)

( * ) Notice: Subject to any disclaimer, the term of this patent is extended or adjusted under 35 U.S.C. 154(b) by 260 days.

(21) Appl. No.: 13/278,562

(22) Filed: Oct. 21, 2011

(65) Prior Publication Data

US 2012/0096955 A1    Apr. 26, 2012

Related U.S. Application Data

(60) Provisional application No. 61/405,963, filed on Oct. 22, 2010.

(51) Int. Cl.
G01L 1/00       (2006.01)
G02B 21/32      (2006.01)
A61B 5/22       (2006.01)

(52) U.S. Cl.
CPC .. G02B 21/32 (2013.01); A61B 5/22 (2013.01)
USPC ..................................................... 73/760

(58) Field of Classification Search
USPC .............................................. 73/760, 862.59
See application file for complete search history.

(56) References Cited

U.S. PATENT DOCUMENTS 5,046,773 A * 9/1991 Modesitt ...................... 294/100
5,413,611 A * 5/1995 Haslam et al. ................ 623/25
5,722,989 A * 3/1998 Fitch et al. ................... 606/205
7,635,844 B2 * 12/2009 Joseph et al. ................ 250/310
8,317,245 B2 * 11/2012 Sun et al. ..................... 294/86.4
2005/0121411 A1   6/2005 Cohen
2008/0237754 A1 * 10/2008 Solomon ...................... 257/414
2009/0149918 A1   6/2009 Krulevitch et al.
2012/0034620 A1   2/2012 Ward et al.

FOREIGN PATENT DOCUMENTS

WO    WO 03/055652 A1    7/2003

OTHER PUBLICATIONS

Fabiato, "Contractions Induced by a Calcium-Triggered Release of Calcium From the Sarcoplasmic Reticulum of Single Skinned Cardiac Cells," J. Physiol. (1975), 249, pp. 469-495.
Iribe, "Force-Length Relations in Isolated Intact Cardiomyocytes Subjected to Dynamic Changes in Mechanical Load," Am J Physiol Heart Circ Physiol 292 (2006), H1487-H1496.

(Continued)

Primary Examiner — Lisa Caputo
Assistant Examiner — Octavia Hollington
(74) Attorney, Agent, or Firm — Alix, Yale & Ristas, LLP

(57) ABSTRACT

The scientific characterization of cellular contractility and cell movement, such as muscle function in particular is, to a large extent, carried out on intact tissue preparations for example using whole intact muscles from animals. Typical indices of muscle function may include isometric force, contractility under external force (load) and spatio-temporal determination of internal calcium concentration under strictly controlled conditions of length and applied force. The major advance of the described apparatus is that the common characterization of cellular contractility can be performed on a single cell rather than an entire tissue or whole animal. As such the apparatus described improves on and eliminates known limitations of currently considered state-of-the-art approaches.

13 Claims, 8 Drawing Sheets

(56) References Cited

OTHER PUBLICATIONS

Tajitsu, "Piezoelectricity of Chiral Polymeric Fiber and Its Application in Biom . . . ," IEEE Transactions on Ultrasonics, Ferroelectrics, and Frequency Control, 55 (5), May 2008.

Brady, "Mechanical Properties of Isolated Cardiac Myocytes," Physiological Reviews, 71 (2), Apr. 1991, pp. 413-428.

Prosser et al., "X-ROS Signaling: Rapid Mechano-Chemo Transduction in Heart," Science (New York, NY) 333 (6048), Sep. 2011, pp. 1440-1445.

* cited by examiner

COMBINATION ULTRASENSITIVE FORCE TRANSDUCER AND GRABBING DEVICE FOR FORCE AND STRAIN MEASUREMENT FROM SINGLE CELLS

CROSS REFERENCE TO RELATED APPLICATION

This application is a nonprovisional application that claims priority under 35 U.S.C. 119(e) from U.S. Provisional Application No. 61/405,963 filed Oct. 22, 2010 for "Combination Ultrasensitive Force Transducer and Grabbing Device for Force and Strain Measurement from Single Cells", the entire disclosure of which is hereby incorporated by reference.

BACKGROUND

The scientific characterization of cell function is often approximated by studying an aggregate structure of cells or the smallest still functional multicellular preparations that retains the function of the entire organ under investigation. When it comes to the quantification of stress or strain on individual cells, technology is limited when it comes to actually measuring stress or strain at such a low force level. It is limited in the ability to impose stress or strain for example in the form of a length change (stretch) or conversely push and then to quantify the response. It is limited in the ability to attach and hold onto a single cell due to the cell's fragile nature. And, it is limited in the ability to manipulate and position the individual cell to allow it to be brought into alignment with a measurement apparatus. This is best illustrated in the case of muscle cells. Muscle function is typically carried out on multicellular intact tissue preparations. During known experimentation, isometric force, contractibility under external force or stretch (often referred to as "load"), with or without electrical stimulation, and temporal determination of membrane potential and/or internal calcium concentration are measured in a strictly controlled environment. Drawbacks of current state of the art equipment for performing measurements on single (individual) muscle cells include:

1. Since tissue preparations do not have blood circulation present, the potential for oxygen deprivation exists as the experimenter approaches the internal portion of the muscle sample. The lack of blood perfusion in isolated tissues results in potential oxygen deprivation due to an increased demand over supply resulting in hypoxia with unknown but usually negative implications on the tissue function. This is directly related to the diffusional limitation in larger intact multi-cellular tissues and whole organs and cannot be completely overcome with high oxygen tension in surrounding fluids.
2. Most known techniques require buffers and experimental reagents which are slow to diffuse toward the center of the muscle sample. Due to the lack of perfusion, experimental substances, salts and ions used to test tissue function will not readily reach all cells in larger tissues and organs, potentially yielding unreliable results and data.

Microscopic analysis of intact muscle preparations is often very difficult. Although optical techniques can be used to observe cells in the outer layer of a tissue, these are also the cells that lie near the injury zone where the tissue sample was separated from the larger unit or organ. Moreover, optical techniques fail to observe and sample responses from the deeper underlying cells.

3. When employing in vivo experimentation techniques, intact organs and tissues thereof are inherently multicellular, leaving the uncertainty that observed behaviors and responses are partly due to complex effects resulting from the contribution of different cells and structures in the same tissues. In other words the measured response is a sum of effects of all cells and supporting structures in the sample. In the case of muscle, these also include cells such as fibroblasts, nerve cells and cells of the blood supply system in the wall of small arteries and capillaries. Also, there is significant connective tissue between the cells (matrix) that greatly influence the passive mechanical properties of a tissue.
4. Diseased muscle has a complex mixture of (dys)functional muscle cells and fibrotic tissue (the remains of dead cells) making it challenging to differentiate between native muscle defects and secondary tissue derived effects on overall tissue contractility such as stiffness and contractile function.

One known method of cell force measurement using force transducers can be found in Addae-Mensah, K. A., *Measurement Techniques for Cellular Biomechanics In Vitro*, Minireview, Society for Experimental Biology and Medicine, p. 792-809, 2008.

It would be advantageous to provide instrumentation and methods for testing force and contraction in single cells, rather than groups of cells.

DRAWINGS

DESCRIPTION

Figure 1:
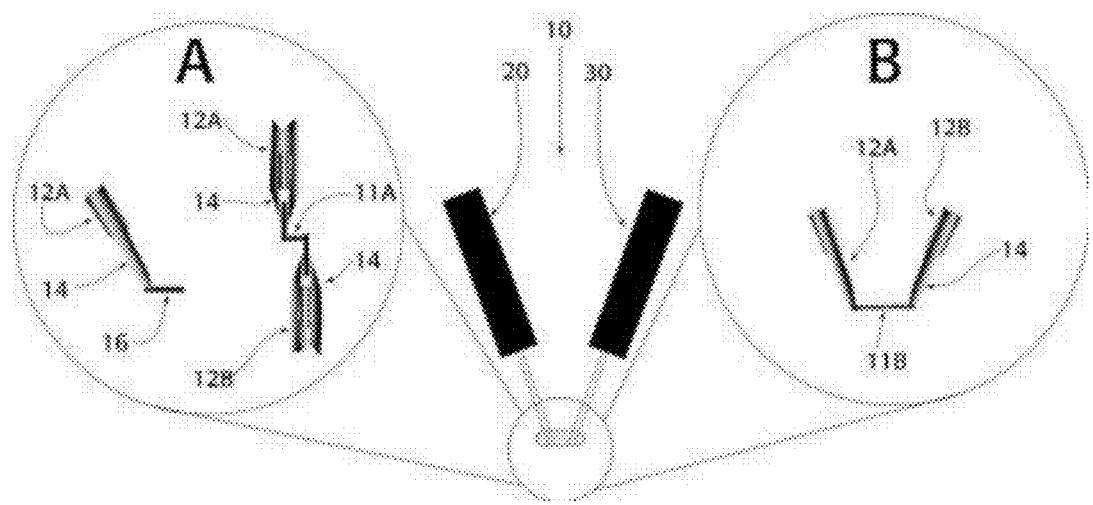
FIGS. 1A and 1B are schematics showing the disclosed system and micro-grabbers.
FIG. 1C is an enlarged schematic showing an embodiment of the disclosed micro-grabbers having a bending piezoactuator.
Figure 1C:
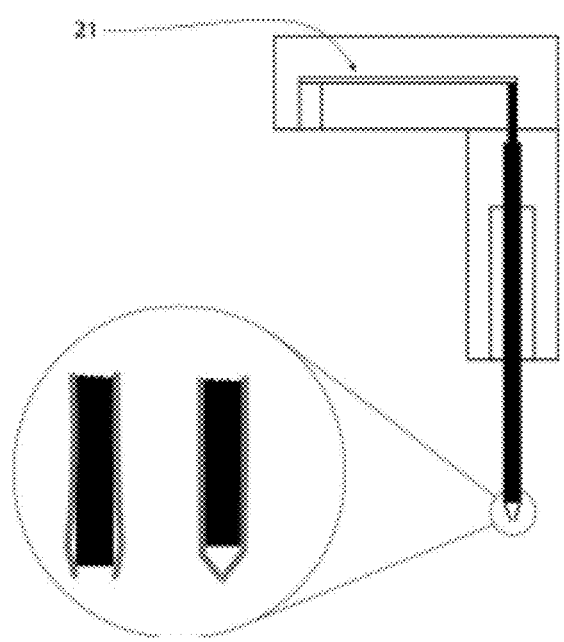

The disclosed method and instrumentation enables evaluation of the function of single isolated cells and provides numerous advantages over those currently employed. Experimenting on single isolated cells (such as muscle cell preparations) eliminates the drawbacks enumerated above. Relevant muscle contraction parameters can be generated and directly measured and evaluated. This enables direct quantification of cellular responses from a single type of cell independent of other cells, thus providing far more reliable data. The instrumentation provides for the combination of a number of components to achieve this goal. The first component is a very sensitive force transducer to quantify, force generated by, stress or strain in a single cell. Second, a piezoactuator (nano-motor) to accurately change the length of a cell (push or pull) or impose an externally controlled variable length change is provided. Third, a cuvette system is included to control the environment of the cell in terms of gas pressures, solutes and nutrition that the cell may need. As part of the experimental paradigm, the cuvette system provides the ability to position and align the cell for attachment to the force transducer and nano motor while retaining the ability to use optical techniques such as, but not limited to microscopy, for further concurrent measurements of cell function. Fourth, a set of miniaturized micro grabbers engineered into the end of the force transducer and nano-motor are necessary to allow these to grab and hold onto cells, with or without the added help of an intermediate holder or use of a biological adhesive substance. The miniaturization with simultaneous optical access the connection between strictly defined muscle contraction conditions and simultaneous microscopically-determined measurement parameters opens up a new and as yet unexplored dimension in cell and muscle research.

Force measurements on single muscle cells preferably employ an ultrasensitive force transducer, which can be reliably calibrated. The force transducer should be sufficiently rigid, as to prevent changes in cell length as a result of contraction and/or not become significantly deformed as a result of cell action during the measurement process, and have a rapid response time in order to follow the cell responses with great fidelity. One suitable transducer is the Scientific Instruments GmbH KG-7 optical force transducer, which has been employed in an embodiment of the disclosed instrument.

An actuator with highly precise axial movement is preferred to investigate cell contraction under load, again without significant self-deformation. The ability to make rapid length adjustments is also preferable to mimic actual real muscle activity situations. These conditions allow changing of cell length in a controlled manner, thus allowing for controlled quantitative mechanical contraction measurements.

The combination of the aforementioned highly isometric force transducer and a rapid, precise actuator enables accurate measurements and analysis. The combination of the two devices allows for multiple experimental modalities relevant to muscle function: the isometric contraction, whereby the cell generates force while kept at a fixed length, the isotonic contraction, whereby the cell is allowed to shorten under a constant stress or load, and the eccentric contraction, whereby the muscle generates force while actively being lengthened by an external force in the opposite direction of its normal shortening. In one embodiment, a Scientific Instruments GmbH piezometric Nano Motor and KG7 optical isometric force transducer are utilized. Such measurements are impossible using known techniques. The closest relevant technique is the carbon fiber method. In the carbon fiber method, the spontaneous adhesion of porous flexible thin carbon fibers is used to attach to a cell. Upon chemical or electrical stimulation, resulting in cell length changes such as contraction or relaxation, or active movement of one of the fibers in order to stretch the cell, the fibers will deform and the deformation of the fiber is calculated back to force if the modulus of the fiber material is known or had been experimentally determined. Muscle force generation and measurements directly coincide with muscle contractions whereby the carbon fibers deform. Consequently, the muscle force and muscle contraction measurements cannot be independently evaluated and are of limited value.

Known techniques do not provide a simple reliable and reversible ability to attach a transducer and/or actuator directly to any single cell whereby the attachment force exceeds the ability of the cell to detach due to its own force-generating ability, which is preferable for such measurements. Incorporated into the disclosed device, the architecture of both transducer and actuator body (the above-mentioned KG7) allows the integration of a micro-grabber device in both the transducer and actuator, thus creating a unique combination of abilities. This unique combination allows the performance of these measurements on single cells and creates a new flexible platform to quantify cell function related to movement and force development. Two optional methods of attachment are employed in the disclosed instrument:

1. Attachment of Cell Ends with Mechanical Micro-grabbers:

Disclosed herein is an embodiment of a micro-grabber, which allows direct attachment to the ends of muscle cells. Preferably, the inventive micro-grabber is configured to open and close via remote control without causing additional movement, which can interfere with measurements. In the disclosed device, this configuration is realized by employment of an open and close mechanism located proximate to the center of the micro-grabber. In a preferred embodiment, this action is generated through a piezoelectric mechanism, which allows for actuation of the grabbers without any manual contact to the force transducer or nano motor. A further characteristic of the micro-grabber is that it is sufficiently sensitive so as not to damage or traumatize the muscle cell ends during attachment. Trauma to the muscle cell end would effectively end any experiment. The piezoelectric mechanism in the disclosed micro-grabber allows for continuous and steady movement of the grabbers, while providing a fine and precise grabbing process that can be stopped at any moment. This allows the clamping force to be controlled efficiently. As embodiments of the grabbers are commonly made of metal, occasional damage to the muscle membrane cannot be avoided in the presence of electrical fields often needed to induce contraction. A non-conducting coating can optionally be applied to the grabbers to minimize this occurrence. Further, if there is weak friction between a muscle cell and micro-grabber, the cell can be susceptible to sliding from the grabber mechanism during contraction experiments. An optional secondary coating or glue like substance can be applied to the micro-grabber arms for improving adhesion of the cell to the grabber.

2. Attachment of Muscle Cells to Glass Rods Coated with Adhesive:

Directly grabbing very short muscle cells, such as cardiomyocytes, with the inventive micro-grabbers can present difficulties. However, it has been found that these types of cells adhere to glass fibers coated with a suitable biocompatible adhesive. The adhesion generated is sufficient for cardiomyocytes, as the forces they generate are somewhat weak, as not to cause detachment from the glass rods. A similar methodology has been used previously, as mentioned above, with adhesion of cells to carbon fiber rods. Often this adhesion was too weak, resulting in spontaneous detachment during experimentation as cells contract. The attachment to the disclosed coated glass rods is significantly stronger, to the point that detachment during cell contraction is significantly reduced or even prevented. In this embodiment, the glass rod (as opposed to the muscle cell end) is grabbed with a micro-grabber, like that discussed above. This procedure significantly simplifies cell attachment to the force transducer and nano motor.

The disclosed instruments and methods of investigating mechanical properties of individual muscle fibers allow the validation of scientific data collected from tissue samples. They also enable combining muscle contraction experiments with experiments only possible on single cells. This substantially widens the possibilities in muscle and cell research.

FIG. 1 is a general schematic diagram of the disclosed combination instrument 10. As depicted, the instrument (10) is configured for both direct attachment of the micro-grabber (12A and 12B) to a cell and attachment via an intermediary.

FIG. 1B depicts an embodiment of the inventive micro-grabbers (12A and 12B) configured for direct attachment with a singular muscle cell. FIG. 1B shows a pair of micro-grabbers (12A and 12B) attached to opposite ends of a single skinned skeletal muscle cell 11B via the respective uncoated grabber tips (14). A specific coating can optionally be applied to the tips (14) as preferred for a particular experiment.

In contrast to skeletal cells, a single heart muscle cell cannot reliably be grasped directly by the grabbers. As depicted in FIG. 1A, the micro-grabbers (12A and 12B) can engage with the opposite ends of the muscle cell (11A) by way of intermediate glass rods (16). The glass rods (16) are typically coated with a material that enhances or affects adherence to the muscle cell (11A). In one embodiment, the muscle cell (11A) is positioned approximately flat on a surface, and the micro-grabbers (10) are positioned at angles of approximately 90° relative to the respective cell (11A) and the surface. This preferred configuration is effective with either attachment method (FIG. 1A or 1B).

The micro-grabbers (12) depicted in FIGS. 1A and 1B are typically operated via a remote control to avoid undesired movement during opening and closing. The grabbers (12) can be gradually opened and closed and the strength of squeezing the cell can be automatically adjusted the experimental needs.

As noted, a force transducer (20) is employed within the disclosed system in operational communication with the micro-grabbers (12). A preferred force transducer (20) for employment in the disclosed system has a resonance frequency of approximately 150 Hz. The force resolution of the transducer is 0.3 µN, and the time resolution of the force measurement is 7 ms using an anti-oscillation filter.

Figure 2:
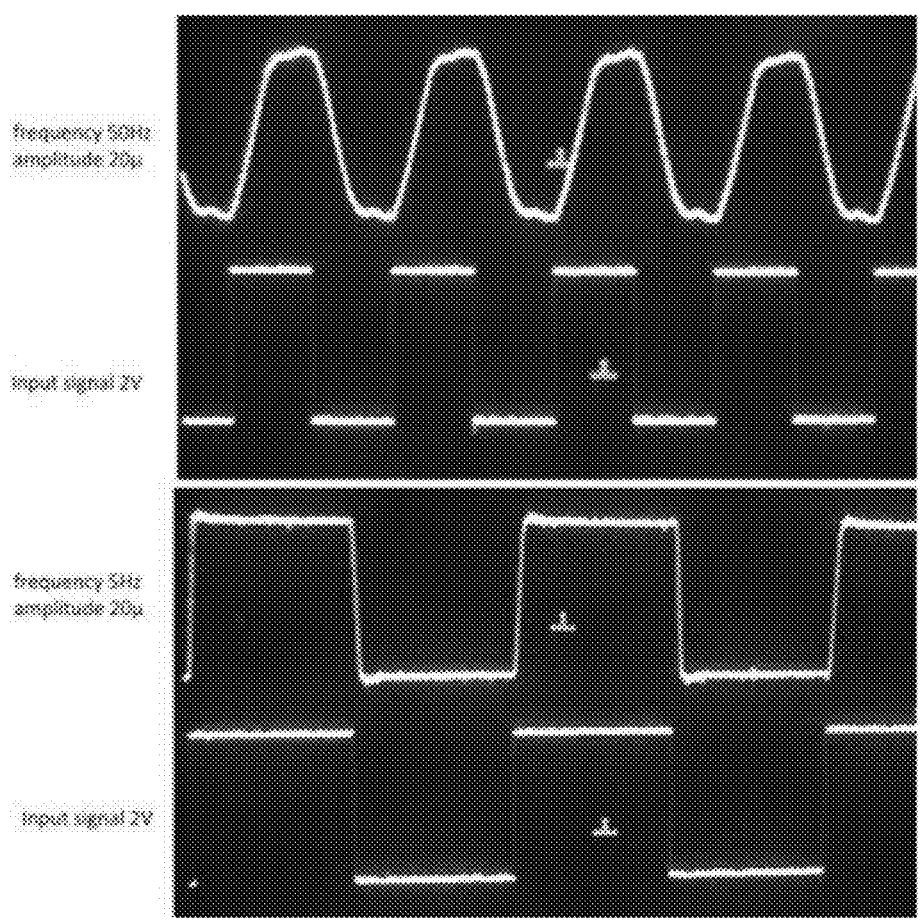
FIG. 2 is a length response output from the nano-motor of the disclosed system.

Similar to the force transducer (20), a nano-motor (30) is engaged with the micro-grabbers (12B) and can be operated similarly. The nano-motor (30) allows and initiates administration of length changes to the subject sample cell to which it is attached. In one preferred embodiment, the spatial resolution of the motor is 20 nm and the maximum range is 80 µm. FIG. 2 depicts an example of the length response output from the nano-motor (30) to rectangular input signals. The position of the nano-motor (30) is feedback controlled which assists in avoiding slow drifts after a position change.

In a preferred embodiment, an electrical control unit is integrated within a cell investigation unit and includes: a bridge amplifier for the force transducer, an anti-oscillation circuit for deriving the resonance oscillation from the force signal and a feedback control for the nano-motor.

Figure 3:
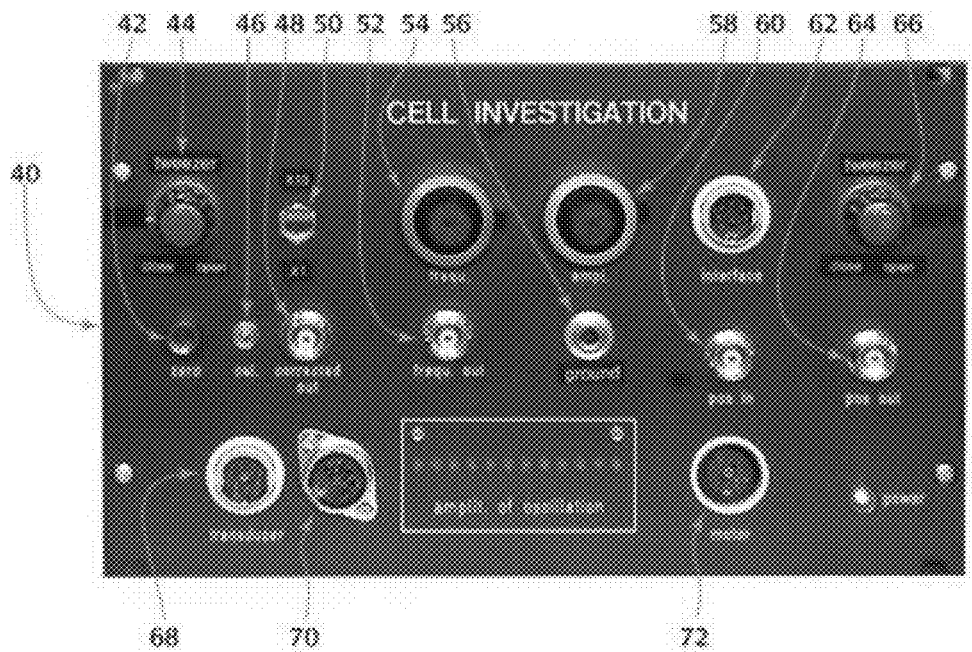
FIG. 3 is a schematic of a cell investigation unit panel for use in the disclosed system.

FIG. 3 shows an embodiment of the cell investigation unit panel (40). A typical operation of the unit includes the following steps: Pressing the "zero" button (42) sets the bridge amplifier to zero volt output. Turning the potentiometer (44) opens and closes the micro-grabbers (12A) of the force transducer. A screwdriver operated potentiometer (46) can be used for calibration of the force signal. The force signal output is depicted as reference numeral 48. The force signal passes an anti-oscillation filter, which is integrated into the unit. If the potentiometer switch (44) is in position X1, 1 volt output corresponds to 100 µN, and if the switch (44) is in position X10 1 volt output corresponds to 10 µN. The switch (50) is used to toggle the amplification of the "corrected" output of the force signal from X10 to X1. This switch is typically disabled if the system is operated by the MUSCLEDATA or MDAC software program (used for automated operation) that can be used to control the motor position via an analog voltage command in input (60). The connector (52) for the magnet assembly will be discussed in further detail. The frequency adjustment of the oscillator driving the magnet assembly is depicted as reference numeral (54). The unit (40) also includes a ground connector (36) for the stimulator. The amplitude of the oscillator frequency driving the magnet assembly is depicted as reference numeral 58. The nano-motor follows an electric signal fed into the input 60. Here, 1 volt input corresponds to the displacement of 10 µm. A connector for the interface for using the operation software MUSCLEDATA or MDAC is shows as reference numeral 62. The displacement of the motor is read from the output 64. 1 volt output corresponds to 10 µm displacement. The potentiometer (66) operates the motor for the micro-grabbers (12B). The force transducer (20) is typically connected to the unit (40) via the connector (68). The photodiode array (70) displays the amplitude of the force transducer oscillation. Finally, the nano-motor can be connected to the unit (20) via the connector (72).

Figure 4:
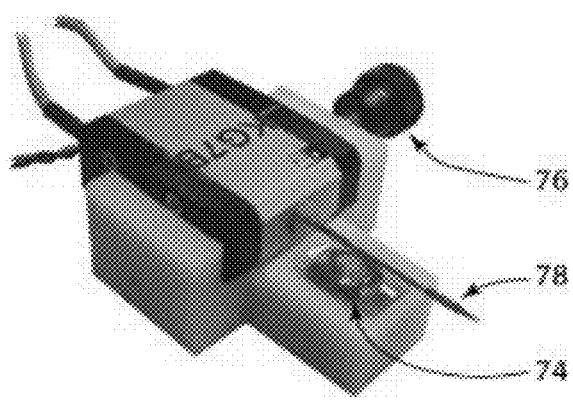
FIG. 4 shows a magnet assembly for use with the force transducer of the disclosed system.

Adjusting the anti-oscillation filter of the force transducer (20) is typically performed by exciting the resonance oscillation of the transducer (20). For this purpose the force transducer is connected to a magnet assembly as shown in FIG. 4. The magnet (74) is arrested via the screw (76). The force transducer pin (78) should typically be permitted to move (i.e., oscillate).

Frequency adjustment: In a preferred method of operation of the disclosed system 10, the instrument is initially set on the highest possible frequency (i.e., the potentiometer "frequ." (54) is turned as far as possible to the right). The amplitude and current is also generally set high (potentiometer "ampl."). The amplitude and current are then slowly reduced, in this embodiment, by a user turning the respective potentiometers counter clockwise. Once the oscillator frequency narrows the resonance frequency of the transducer, the transducer will begin oscillating. The oscillations become visible on the LED array (70) as flickering. As the resonance frequency of the transducer is approached, the level of oscillation increases such that the LED array appears fully lit or close to fully lit. The amplitude can then be decreased with the potentiometer "ampl." (58) to levels below LED saturation.

The above-described frequency adjustment procedure is typically repeated until a clear maximum oscillation is identified at a certain adjustment of the potentiometer "frequ." (54). The potentiometer (54) is then arrested in the aforementioned position of maximum oscillation. The more accurately that the frequency of the anti-oscillation unit is adjusted to the resonance frequency of the force transducer (20), the better the ringing phenomenon of the force transducer is derived from the force signal, yielding more accurate results.

Additionally, the resonance oscillation of the transducer (20) is evoked, if the adjusted frequency of the anti-oscillation unit is set at half of the resonance frequency of the force transducer (20). The filter also operates sufficiently with half of the resonance frequency, but the time resolution of the force measurement is reduced by half. The highest frequency is preferable, which evokes resonance oscillation.

Figure 5:
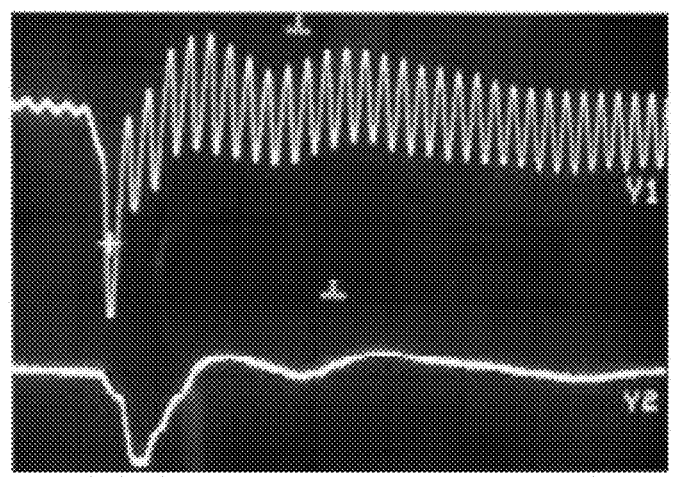
FIG. 5 shows a force transient obtained from the bridge amplifier output of the disclosed system.

FIG. 5 depicts a force transient obtained directly from the bridge amplifier output (upper trace), and after passing the "anti oscillation" unit (lower trace). In the upper trace a steady resonance frequency is superimposed on the actual force transient. After passing the anti-oscillation circuitry, this resonance signal is removed. Remaining is the force transient generated by the cell and measured by the force transducer.

Figure 6:
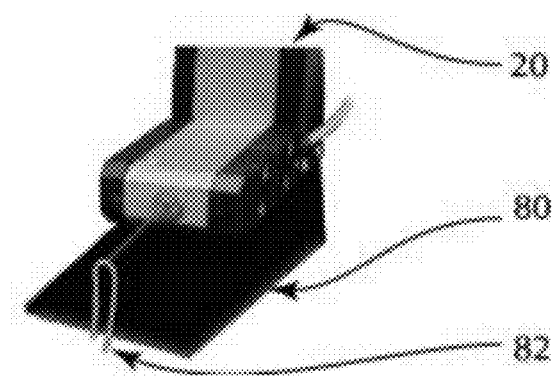
FIG. 6 depicts the force transducer of the disclosed system mounted to a calibration stand.

Calibration of the force transducer: In a typical calibration of the force transducer (20), the cell investigation unit (40) is first disconnected from the any external signal recording devices. The amplification switch (50) for toggling between X1 and X10 on the front panel of the instrument is switched to the X1 position. The transducer (20) is typically mounted on a calibration stand (80), as shown in FIG. 6. After the output voltage is set to zero with the "zero" pushbutton (42), a weight (82) of a predetermined mass (in one embodiment, approximately 80 mg) is hung from the tip of the transducer (20). This is shown in FIG. 6. The screwdriver operated potentiometer "cal." (46) is set so the output voltage at the BNC corrected out shows the corresponding voltage (for example, set to 8V for 80 mg or 800 μN). This calibration procedure is typically employed when the force of the weight (82) acts generally perpendicularly on the transducer pin (78), like the illustration in FIG. 6. When the angle differs from 90°, the output signal can be adjusted accordingly to correct for the angle.

Figure 7:
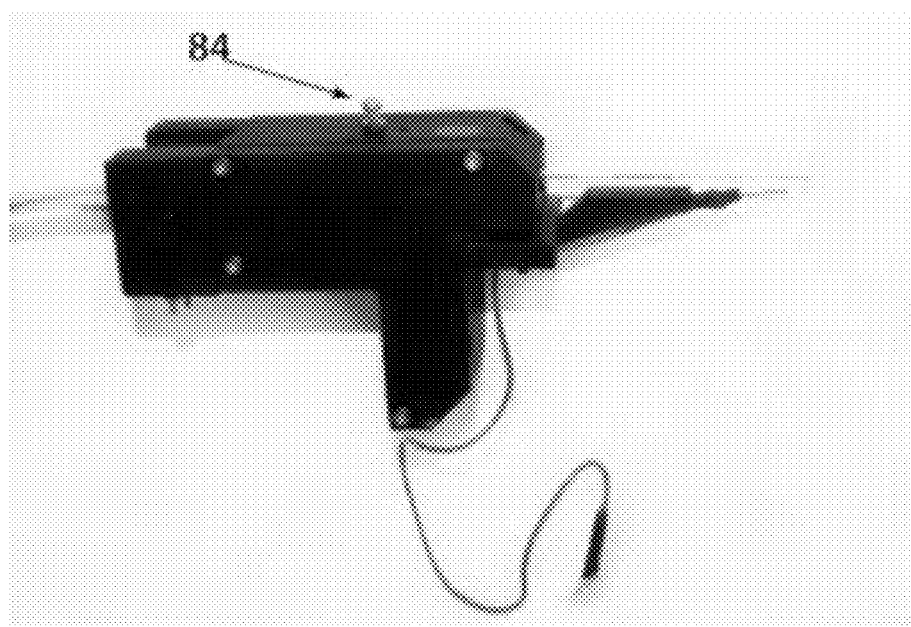
FIG. 7 depicts an embodiment of the nano-motor of the disclosed system.

Realignment of the mechanical zero position of the nano-motor: If the displacement range of the nano-motor (30) is limited, the mechanical zero position of the motor may be left unadjusted. To readjust, the switch "motor adj."—"normal" (in this embodiment, located on the rear of the cell investigation unit (40)) is turned into the position "motor adj." (not depicted). The position of the motor (30) at the BNC plug "pos. out" (64) is typically measured on the front panel of the unit (40). If the position differs substantially from 0 volts, the screw (84) (see FIG. 7) can be turned to adjust the output to 0 volts. Switching the switch for toggling between "motor adj." and "normal" back to the "normal" position returns the instrument to the normal (i.e. feedback) controlled operation mode.

Point stimulation of the preparation: The micro-grabbers (12A) of the force transducer (20) are typically electrically grounded. Muscle cells need an electrical pulse or stimulation to initiate contraction. This is done with a laboratory stimulator. Typically the ground or (−) output of the stimulator can be electrically connected to the ground plug (56) on the front panel of the cell investigation unit (40). Here, the micro-grabbers (12B) of the motor are electrically connected to the banana plug "stimulator" on the rear of the unit (40). The stimulator's other output, typically (+) can be connected to that banana plug. Together, this forms an electrical circuit to stimulate the cell.

Figure 8:
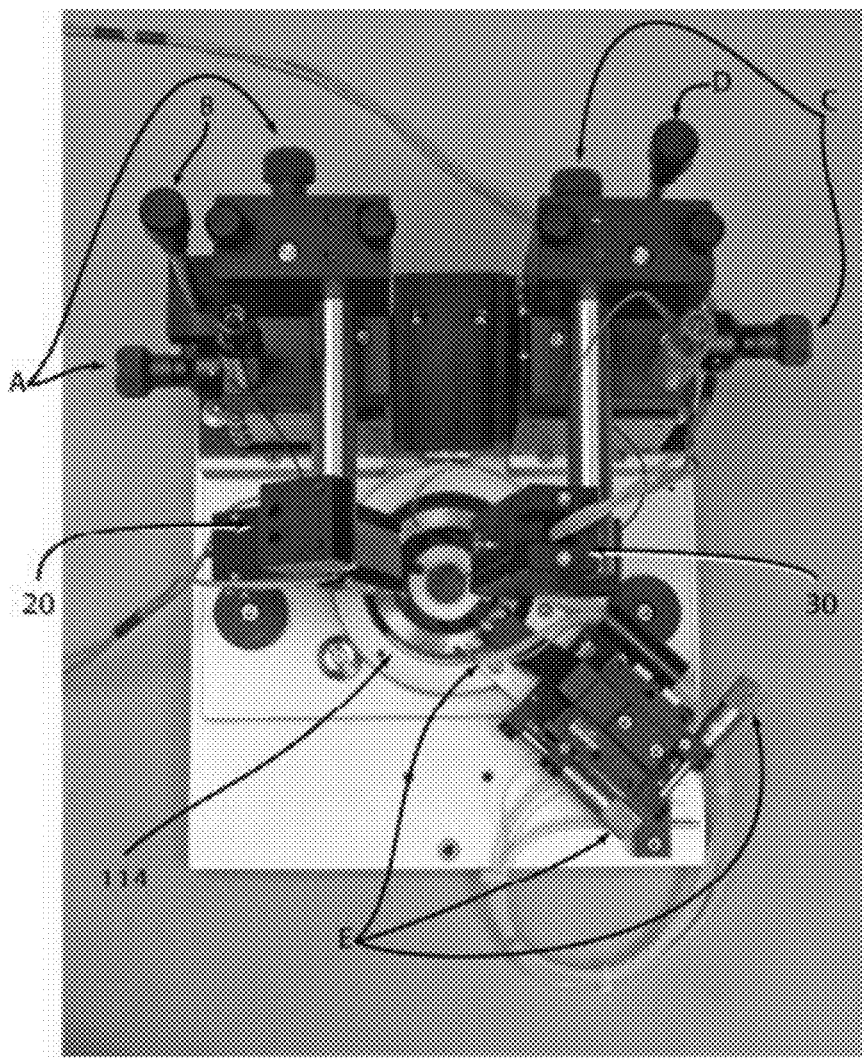
FIG. 8 depicts a preferred embodiment of a cuvette unit in engagement with the disclosed system.

FIG. 8 depicts a cuvette system (114) for use within the disclosed system (100. In the depicted cuvette system, the A arrows indicate the X-Y-Z alignment and the B arrow indicates the vertical fine adjustment of the force transducer 20. The C arrows indicate the X-Y-Z alignment and the D arrow indicates the vertical fine adjustment of the nano-motor (30). The described A, B, C and D indicated adjustment is related to the stationary microscope and independent of the positioning of the cuvette system (114). Thus, the force transducer (20) and nano-motor (30) are adjusted with respect to the optical axis of the microscope. The E arrows indicate the adjustment of the cuvette system itself. In typical operation, the cuvette system (114) is first aligned with the microscope structure such that the optical axes of each align. When a cell is then positioned in the center of the cuvette, it is also automatically in the center of the optical axis of the microscope. This configuration allows rotation of the table to initiate rotation of the observed preparation (i.e., muscle sample or cell) around the optical axis of the microscope independent of the position of the cuvette (114). This is a very inventive solution to properly align a cell with the instrument prior to attachment to the force transducer and nano-motor.

Grasping the glass rods: As previously noted, FIG. 1A shows an embodiment of the disclosed device that includes glass rods (16) or like elements which are gripped by the micro-grabbers (12A and 12B), and then attached via adhesive to a muscle cell sample (16). A typical arrangement of this embodiment would first include the step of maneuvering the cuvette (114) such that the micro-grabbers (12A or 12B) of the force transducer (20) or the nano-motor (30) are positioned above the subject glass rod (16). The positioning of the glass rod (16) can be altered by turning the rotating table. The micro-grabbers are opened by remote operation of the embedded motor, then can be lowered into position with the Z-control of the nano-motor (or the transducer) until the micro-grabbers (12A or 12B) contact a cover slip that can be positioned beneath the glass rod (16) and typically forms the bottom of the experimental chamber or cuvette. The micro-grabbers can then be closed to grip the rod (16), and then elevated accordingly with the corresponding fine adjustment.

Figure 9:
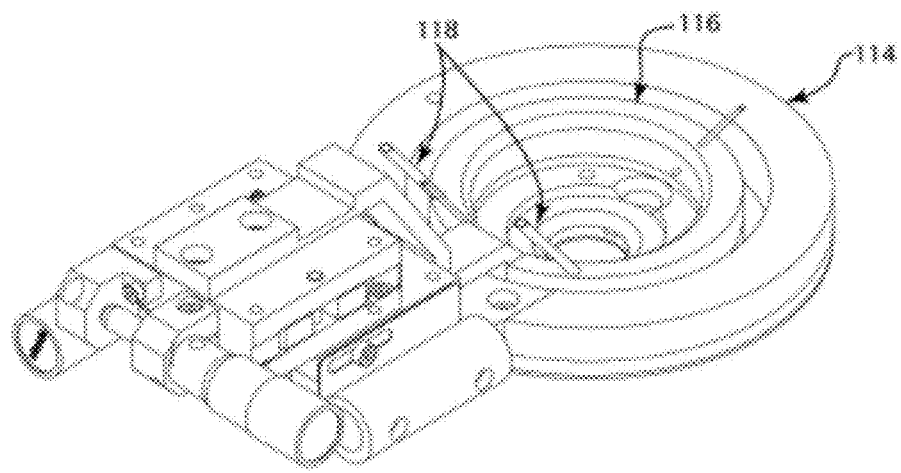
FIG. 9 is an exploded view of the cuvette unit of FIG. 13.

FIG. 9 shows an isolated view of a cuvette (114). The cuvette (114) can be typically cleaned by first removing the motor (30) and the force transducer (20) from the combination system, as shown in FIG. 8. The cuvette cover (116) is then unscrewed and removed, typically via the handle (118). The cover slip (120) and any other elements can then be cleaned or replaced.

One method of stimulating a muscle sample is via direct stimulation by the micro-grabbers (12A). The micro-grabbers (12A) are connected to the force transducer (20) and are electrically grounded. In one embodiment, the front panel of the cell investigation unit (40) includes a ground plug (56) for grounding the micro-grabbers (12A). The side of the micro-grabbers (12A) that are operatively connected to the operating motor are connected via banana plug on the rear of the cell investigation unit (40). The plug is operatively connected to the other output of the stimulator. The current for stimulation of the muscle sample flows via the micro-grabbers (12A).

Figure 10A:
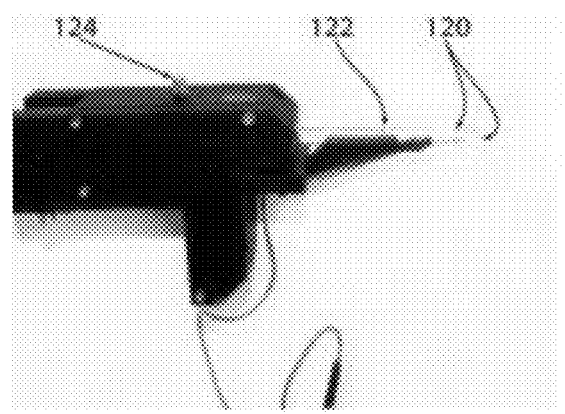
FIGS. 10A and 10B depict an embodiment of the disclosed system which utilizes electrodes for stimulation of a muscle sample.
Figure 10B:
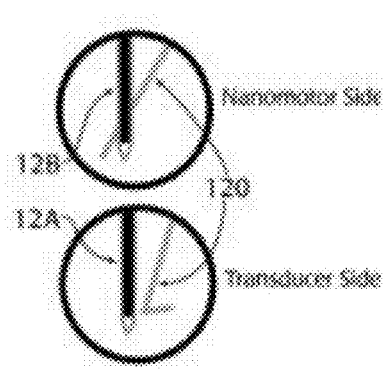

Additionally, the disclosed system (10) allows for stimulation of a muscle sample via separate electrodes. A preferred embodiment employs platinum electrodes. With reference to FIGS. 10A and 10B, the electrodes (1200 are rigidly retained by the holder (122) via engagement of a screw (124"S"). A platinum wire (126) is slipped into the holder (122), as shown. Alignment of the electrodes (120) is then achieved by manipulation of the platinum wire (126). The electrode should be located behind the micro-grabbers (12A and 12B) on both the transducer (20) and nano-motor sides (30), as shown in enlarged FIG. 10B.

Figure 11:
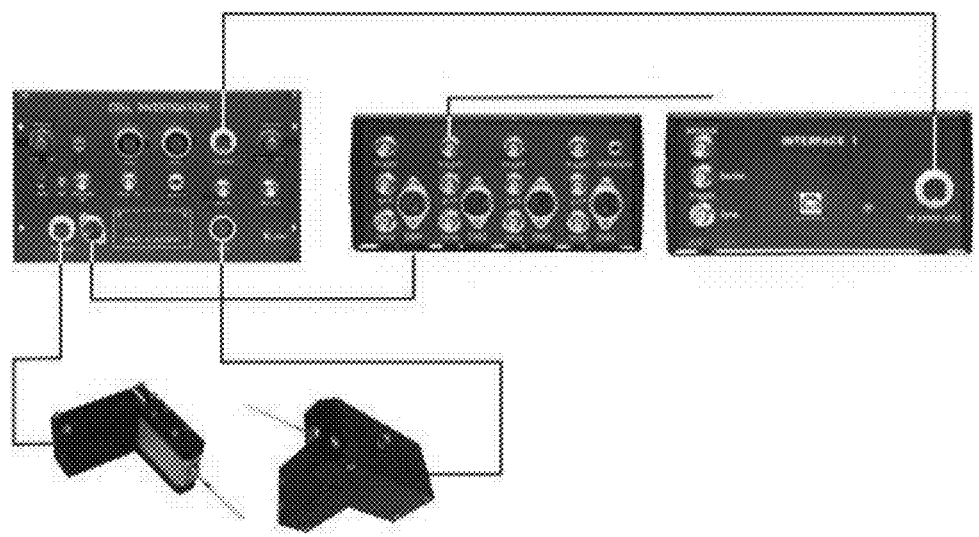
FIG. 11 is a schematic depiction of a typical wiring setup of the disclosed system.

A schematic diagram of a typical wiring setup for the disclosed instrument is shown in FIG. 11.

While a preferred embodiment has been set forth for purposes of illustration, the foregoing description should not be deemed a limitation of the invention herein. Accordingly, various modifications, adaptations and alternatives may occur to one skilled in the art without departing from the spirit of the invention and scope of the claimed coverage.

What is claimed is:

1. An instrument for measuring internal force and strain within a single cell comprising:
   a micro-grabber assembly configured for attachment to a single cell having at least one micro-grabber for gripping at least one connector element configured for attachment to a portion of said single cell;
   a bath system with a stage that is rotatable about an axis and axially reciprocable for assisting in location and alignment of a cell positioned thereon into position for attachment of the cell to the micro-grabber assembly without movement of the micro-grabber and connector element;

a force transducer communicatively connected to the micro-grabber assembly for measuring substantially isometric force and measuring internal force within the single cell to which said micro-grabber assembly is attached when the cell is manipulated via piezoelectric movement of at least one micro-grabber and connecting member to which a portion of the cell is attached.

2. The instrument of claim 1, wherein the micro-grabber assembly comprises two separate micro-grabbers, each micro-grabber gripping a separate connector element, each connector element being configured for independent selective communicative attachment to a portion of a single cell.

3. The instrument of claim 2, wherein each micro-grabber comprises a piezoelectric element which allows for actuation of said grabber independent of manual contact with said force transducer.

4. The instrument of claim 2, comprising a non-conductive coating on each connector element.

5. The instrument of claim 2, wherein each micro-grabber and connector element is made of a non-conductive material.

6. The instrument of claim 2, wherein movement of each of the at least one micro-grabber is operated by a piezoelectric mechanism associated therewith.

7. The instrument of claim 1, wherein a piezoelectric element is cooperatively connected to the micro-grabber assembly and a nano-motor configured for initiating oscillation of each piezoelectric element to move the respective micro-grabber.

8. The instrument of claim 1, comprising a nano-motor communicatively connected to the micro-grabber assembly configured such that operation of said nano-motor causes the micro-grabber to effect a change in the length of a single cell to which the micro-grabber is attached.

9. The instrument of claim 8, wherein the micro-grabber assembly comprises two separate micro-grabbers, each micro-grabber configured for independent selective communicative attachment to a separate connector element, each connector element being attachable to an opposite end of a single cell, and the nano-motor and transducer are each operatively connected to a different micro-grabber.

10. The instrument of claim 1, wherein each connector element is coated with an adhesive to aid in attachment to the single cell.

11. The instrument of claim 1, comprising a nano-motor operatively connected to the micro-grabber element, wherein operation of the nano-motor initiates the micro-grabber element to affect a response in the cell to which the micro-grabber element is attached.

12. The instrument of claim 11, wherein the response in the cell is selected from a group consisting of vibration, length change, pushing and pulling.

13. The instrument of claim 1, wherein the force measurements are within the order of nanograms.

* * * * *